(12) United States Patent
Hashida et al.

(10) Patent No.: US 9,133,748 B2
(45) Date of Patent: Sep. 15, 2015

(54) CONTROL APPARATUS OF INTERNAL COMBUSTION ENGINE

(75) Inventors: Tatsuhiro Hashida, Susono (JP); Hiroki Nishijima, Shizuoku-ken (JP)

(73) Assignee: Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 0 days.

(21) Appl. No.: 14/353,498

(22) PCT Filed: Oct. 26, 2011

(86) PCT No.: PCT/JP2011/074679
§ 371 (c)(1),
(2), (4) Date: Apr. 23, 2014

(87) PCT Pub. No.: WO2013/061421
PCT Pub. Date: May 2, 2013

(65) Prior Publication Data
US 2014/0305106 A1 Oct. 16, 2014

(51) Int. Cl.
*F01N 11/00* (2006.01)
*F01N 3/20* (2006.01)
(Continued)

(52) U.S. Cl.
CPC .............. *F01N 3/2066* (2013.01); *F01N 3/023* (2013.01); *F01N 9/00* (2013.01); *F01N 13/008* (2013.01); *F02D 41/1494* (2013.01); *G01N 15/0606* (2013.01); *G01N 15/0656* (2013.01); *F01N 3/035* (2013.01); *F01N 11/00* (2013.01); *F01N 13/009* (2014.06); *F01N 2550/04* (2013.01); *F01N 2560/05* (2013.01);
(Continued)

(58) Field of Classification Search
CPC ....... F01N 3/035; F01N 3/2066; F01N 11/00; F01N 13/008; F01N 13/009; F01N 2550/04; F01N 2560/05; F01N 2560/20; F01N 2610/02; F01N 2900/0416; F01N 2900/0418; F01N 2900/0421; F01N 2900/1616; F02D 41/1466; F02D 41/1494; F02M 25/07
USPC ........... 60/276, 277, 278, 286, 295, 297, 301, 60/311, 320
See application file for complete search history.

(56) References Cited

U.S. PATENT DOCUMENTS 8,627,645 B2 * 1/2014 Hopka et al. .................... 60/276

FOREIGN PATENT DOCUMENTS

JP 2009-144577 7/2009

*Primary Examiner* — Thomas Denion
*Assistant Examiner* — Jorge Leon, Jr.
(74) *Attorney, Agent, or Firm* — Finnegan, Henderson, Farabow, Garrett & Dunner, LLP

(57) ABSTRACT

An SCR system (8) is arranged in an exhaust path (4) of an internal combustion engine (2) to which the invention is applied, and a particulate filter (14) is arranged downstream thereof. A control apparatus (16) includes temperature controlling means for controlling a temperature of an element portion of the particulate sensor. The temperature controlling means performs control to increase the temperature of the element portion of the particulate sensor to a first temperature range (T1), when a cumulative value (t) of a time for which the particulate sensor is used in a specific operating state reaches a reference time (t1), after detection of a particulate amount by the particulate sensor has started this time. Here, the specific operating state is an operating state set taking into account an operating state in which urea related substances tend to be discharged to a downstream side of the SCR system (8). Also, the first temperature range (T1) is a temperature that is higher than a temperature at which the urea related substances decompose, and lower than a temperature at which the particulates are burned off.

7 Claims, 5 Drawing Sheets

(51) Int. Cl.
*F02D 41/14* (2006.01)
*F01N 3/023* (2006.01)
*G01N 15/06* (2006.01)
*F01N 9/00* (2006.01)
*F01N 3/035* (2006.01)
*F01N 13/00* (2010.01)
*F02M 25/07* (2006.01)

(52) U.S. Cl.
CPC ........ *F01N 2560/20* (2013.01); *F01N 2610/02* (2013.01); *F01N 2900/0416* (2013.01); *F01N 2900/0418* (2013.01); *F01N 2900/0421* (2013.01); *F01N 2900/1616* (2013.01); *F01N 2900/1812* (2013.01); *F01N 2900/1821* (2013.01); *F02D 41/1466* (2013.01); *F02M 25/07* (2013.01); *Y02T 10/24* (2013.01); *Y02T 10/47* (2013.01)

CONTROL APPARATUS OF INTERNAL COMBUSTION ENGINE

CROSS-REFERENCE TO RELATED APPLICATIONS

This application is a national phase application of International Application No. PCT/JP2011/074679, filed Oct. 26, 2011, the content of which is incorporated herein by reference.

TECHNICAL FIELD

The invention relates to a control apparatus of an internal combustion engine. More specifically, the invention relates to a control apparatus that controls an internal combustion engine provided with a particulate sensor in an exhaust path.

BACKGROUND ART

For example, a PM sensor (particulate sensor) for detecting particulates (particulate matter; hereinafter also referred to as "PM") in an exhaust path of an internal combustion engine is arranged in a system of Patent Document 1. This PM sensor includes an insulating substrate, and a pair of electrodes arranged above the insulating substrate and spaced apart from each other.

If PM in exhaust gas accumulates between the pair of electrodes of this PM sensor, the conductivity between the electrodes will change. There is a fixed correlation between the accumulated PM amount and the conductivity between the electrodes, and the resistance between the electrodes changes according to the PM accumulation amount between the electrodes. Also, there is a correlation between the PM amount accumulated between the electrodes and the PM amount in the exhaust gas. Therefore, the PM amount in the exhaust gas is detected by detecting a resistance value between the electrodes of the PM sensor.

With the technology in Patent Document 1, the PM sensor is arranged downstream of a particulate filter (Diesel Particulate Filter; hereinafter also referred to as "DPF"). In Patent Document 1, a determination of whether there is a failure of the DPF or the like is made by detecting the PM amount discharged downstream of the DPF, based on the resistance value between the electrodes of the PM sensor.

PRIOR ART DOCUMENTS

Patent Documents

Patent Document 1: Japanese Patent Application Publication No. 2009-144577

SUMMARY OF THE INVENTION

Problems to be Solved by the Invention

There is a system in which a urea SCR (Selective Catalyst Reduction) system for purifying NOx is arranged in an exhaust path of an internal combustion engine, and a PM sensor is arranged downstream thereof in the SCR system, urea aqueous solution is supplied by injection into the exhaust path, and the NOx is reduced by a catalyst, by ammonia that is produced from the urea aqueous solution.

However, there are cases in which the supplied urea and substances derived from urea (hereinafter, also referred to as "urea related substances" that include area and substances derived from urea) pass through the SCR system and is discharged on the downstream side. When the urea related substances discharged downstream adhere to electrodes of the PM sensor, it causes the resistance value between the electrodes of the PM sensor to change. As a result, variation may occur in the output of the PM sensor, and the sensitivity of the PM sensor may decrease. This variation in output and decrease in sensitivity of the PM sensor may bring about a situation in which an erroneous determination occurs in a failure determination of the DPF, for example, and are thus not desirable.

It is an object of the invention to solve the foregoing problems, so the invention provides an improved control apparatus of an internal combustion engine, which suppresses an effect from urea related substances adhering to electrodes of a PM sensor, so as to be able to perform a failure determination of the DPF and detect a PM amount with higher accuracy.

Means for Solving the Problems

In order to accomplish the foregoing object, the invention is a control apparatus that controls an internal combustion engine in which a SCR system is arranged in an exhaust path and a particulate sensor is arranged downstream thereof, which includes particulate detecting means for detecting an amount of particulates derived from operation of the internal combustion engine, inside of the exhaust path, based on an output of the particulate sensor, and temperature controlling means for controlling a temperature of an element portion of the particulate sensor. The temperature controlling means performs control to increase the temperature of the element portion of the particulate sensor to a first temperature range when a cumulative value of a time for which the particulate sensor is used in a specific operating state reaches a reference time, after detection of the particulate amount by the particulate sensor has started this time.

Here, the specific operating state is an operating state set taking into account an operating state in which urea related substances tend to be discharged to a downstream side of the SCR system. A state in which an intake air amount is large, a state in which a urea equivalent ratio is high, and a state in which the temperature of a catalyst is low, and the like, are examples of the operating state in which urea related substances tend to be discharged.

Also, the first temperature range is a temperature that is higher than a temperature at which the urea related substances decompose, and lower than a temperature at which the particulates are burned off.

In this invention, when a particulate filter for trapping the particulates in the exhaust gas is arranged upstream of the particulate sensor in the exhaust path of the internal combustion engine, the control apparatus of an internal combustion engine may also be provided with means for prohibiting a predetermined control related to the particulate filter, until the temperature of the element portion reaches the first temperature range. Alternatively, the control apparatus of an internal combustion engine may also be provided with means for starting a predetermined control related to the particulate filter, after the temperature of the element portion has reached the first temperature range.

In these cases, the predetermined control is preferably failure determining control that determines whether there is a failure in the particulate filter, based on the output of the particulate sensor.

Also in this invention, the temperature controlling means may perform control to increase the temperature of the element portion, when the internal combustion engine is in an operating state in which the amount of the particulates discharged is less than a reference amount.

Also in this invention, when an EGR (Exhaust Gas Recirculation) system is provided, means for stopping recirculation of exhaust gas by the EGR system when a change in a load during operation of the internal combustion engine is larger than a predetermined change may also be provided.

Also in this invention, means for limiting an accelerator opening amount change amount to within a predetermined range that is smaller than a normal change amount of an accelerator opening amount, when a change in a load during operation of the internal combustion engine is larger than a predetermined change may also be provided.

Effect of the Invention

When the particulate sensor, is used to a certain degree in a specific operating state in which urea related substances tend to be discharged, the urea related substances adhere to the element portion of the particulate sensor, so variation may occur in the output of the particulate sensor. In this regard, according to the invention, control to increase the temperature of the element portion to the first temperature range is executed when the particulate sensor has been used to a certain degree in a specific operating state. In this control, the first temperature range is a temperature that is higher than a temperature at which urea related substances decompose, and a temperature that is lower than a combustion temperature of the particulates. Therefore, the urea related substances are removed while leaving the particulates that are adhered to the element portion. As a result, the effect from the adherence of urea related substances is able to be suppressed, so more accurate output of the particulate sensor according to the particulate amount is able to be obtained.

Also, in the invention, control related to the particulate filter may be executed after more accurate output of the particulate sensor is obtained, when means for prohibiting a predetermined control related to the particulate filter until the temperature of the element portion reaches the first temperature range is provided, or when means for starting a predetermined control after the temperature of the element portion has reached the first temperature range is provided. Therefore, the control of the particulate filter can be executed with higher accuracy.

From the control described above, particulates may tend not to adhere to the element portion when the element portion is in the first temperature range, compared to when the element portion is in a normal state. In this regard, in this invention, if control to increase the temperature of the element portion is performed when the operating state is one in which the amount of particulates discharged is less than a reference amount, a decrease in sensitivity of the particulate sensor due to the temperature increase of the element portion described above can be suppressed, so more accurate output of the particulate sensor is able to be obtained.

MODES FOR CARRYING OUT THE INVENTION

Figure 1:
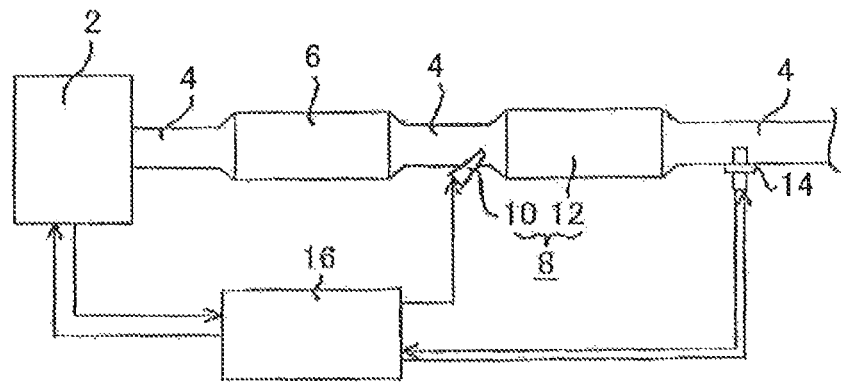
FIG. 1 is a view showing a frame format illustrating the overall structure of a system of example embodiments of this invention.

Hereinafter, example embodiments of the invention will be described with reference to the drawings. In the drawings, like or corresponding portions will be denoted by like reference numerals, and descriptions thereof will be simplified or omitted.

First Example Embodiment

Overall Structure of the System of the First Example Embodiment

FIG. 1 is a view illustrating the overall structure of a system of a first example embodiment of this invention. The system in FIG. 1 is used mounted in a vehicle or the like. In the system shown in FIG. 1, a DPF (Diesel Particulate Filter) 6 that is a particulate filter is arranged in an exhaust path 4 of an internal combustion engine 2. The DPF 6 is a filter that traps particulates (PM; particulate matter) that is particulate matter included in exhaust gas.

A urea SCR system 8 (hereinafter, also referred to as "SCR system") is arranged downstream of the DPF 6 in the exhaust path 4. The SCR system 8 includes an injection valve 10 for urea aqueous solution, which is arranged in the exhaust path 4, and a selective reduction type NOx catalyst 12 (hereinafter, also simply referred to as "NOx catalyst") arranged downstream of the injection valve 10 in the exhaust path 4. The injection valve 10 is connected to a urea aqueous solution tank, not shown, and injects urea aqueous solution into the exhaust path 4 upstream of the NOx catalyst 12. As will be described later, the injected urea aqueous solution decomposes and ammonia is produced. The NOx catalyst 12 purifies the exhaust gas by reducing the NOx in the exhaust gas using the ammonia as a reducing agent. A PM sensor 14 (particulate sensor) is arranged downstream of the NOx catalyst 12.

This system is provided with a control apparatus 16. In addition to the PM sensor 14, various sensors of the internal combustion engine 2 are connected to an input side of the control apparatus 16. Also, the injection valve 10 and an electric circuit of the PM sensor 14 of the internal combustion engine 2, as well as various actuators, are connected to an output side of the control apparatus 16. The control apparatus 16 executes a predetermined program based on input information from the various sensors, and executes a variety of controls related to operation of the internal combustion engine 2, by activating the various actuators and the like.

Figure 2:
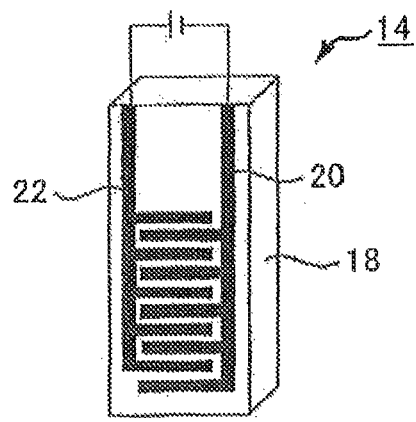
FIG. 2 is view showing a frame format illustrating the structure of an element portion of a PM sensor of the example embodiments of this invention.

FIG. 2 is a view showing a frame format illustrating the structure of an element portion of the PM sensor 14 of the first example embodiment. As shown in FIG. 2, the element portion of the PM sensor 14 has an insulating substrate 18. A pair of electrodes 20, 22 are formed on a surface of the insulating substrate 18. The pair of electrodes 20, 22 are arranged a fixed distance apart in a state not contacting each other. The electrodes 20, 22 each have a portion formed in a comb teeth shape, and are formed so as to mesh with each other at this portion. In the first example embodiment, the electrodes 20, 22 having the comb teeth shape are illustrated, but the invention is not limited to this kind of shape. The pair of electrodes need only face each other. A heater, not shown, is embedded in a lower layer of the electrodes 20, 22 inside the insulating substrate 18.

The pair of electrodes 20, 22 are connected to a power supply (not shown) via an electric circuit or the like. Consequently, high voltage is applied between the electrode 20 and the electrode 22. Also, the heater is connected to a power supply (not shown) via an electric circuit or the like, and consequently, a predetermined power is supplied to the heater, and as a result, the element portion is heated. The supplying of these powers is controlled by the control apparatus 16.

Summary of Control of the First Example Embodiment

In the first example embodiment, control of detection of the PM amount, resetting of the PM sensor 14, failure determination of the DPF 6, and regeneration of the DPF 6, that will be described below, is included in the control performed by the control apparatus 16.

In the example embodiment described below, PM that is to be trapped by the DPF 6 and that is to be measured by the PM sensor 14 refers to particulate matter discharged from the internal combustion engine 2 by operation of the internal combustion engine 2, such as Ash (soot) derived from lubricant, and matter derived from combustion of the internal combustion engine such as soot (soot-like matter such as carbon) and SOF (Soluble Organic Fraction; soluble organic fraction).

(1) Detection of the PM Amount

When detecting the PM discharge amount, a "trapping voltage" that is high voltage for trapping PM is applied between the electrodes 20, 22. When the trapping voltage is applied between the electrodes 20, 22, PM in the exhaust gas is trapped and accumulates between the electrodes 20, 22. As the PM that accumulates between the electrodes 20, 22 increases, the conductive locations between the electrodes 20, 22 increase, and the resistance value between the electrodes 20, 22 becomes smaller. Here, an electrical property having a correlation with the resistance between the electrodes 20, 22 is detected as a sensor output of the PM sensor 14. The PM amount that accumulates on the electrodes 20, 22 is thought to change in conjunction with a change in the PM amount included in the exhaust gas. Therefore, the PM amount in the exhaust gas is detected according to the output of the PM sensor 14. In the example embodiment below, a case in which the sensor output becomes larger as the PM accumulation amount between the electrodes 20, 22 increases will be described for descriptive purposes.

(2) PM Resetting (Control to Burn off Particulates)

The output of the PM sensor 14 increases as the PM accumulation amount between the electrodes 20, 22 increases. However, when the accumulation amount between the electrodes 20, 22 reaches a threshold limit, the output of the PM sensor 14 will no longer change anymore. In this state, the PM sensor 14 is no longer able to generate output according to the PM amount in the exhaust gas. Therefore, at a predetermined timing, it is necessary to once remove the PM that is accumulated on the element portion. A process to remove this PM will also be referred to as "PM resetting".

When PM resetting is performed, the control apparatus 16 supplies a predetermined power to the heat of the PM sensor 14, and superheats the element portion of the PM sensor 14 to a temperature at which the PM will be burned off. As a result, the PM that has adhered to the element portion of the PM sensor 14 is burned off. Here, the temperature of the element portion during the PM resetting period is higher than 500° C., and more preferably higher than 700° C. Alternatively, a target temperature of the element portion during the PM resetting period may be set higher than 500° C., and more preferably higher than 700° C., and power may be supplied to the heater. The temperature at which PM burns is approximately 500° C. to approximately 650° C., so if the resetting temperature is made equal to or higher than 700° C. (preferably 700° C. to 800° C.), the reliability that the PM will burn is able to be increased.

(3) Failure Determination of the DPF

If the DPF 6 fails, the PM discharge amount that slips through the DPF 6 and is discharged downstream of the DPF 6 will increase. Therefore, it there is a failure in the DPF 6, the PM accumulation amount that accumulates between the electrodes 20, 22 of the PM sensor 14 will gradually increase, and the sensor output will become larger. Therefore, a failure determination of the DPF 6 can be made based on the sensor output.

More specifically, in the first example embodiment, the control apparatus 16 detects the output of the PM sensor 14 after a predetermined period of time has elapsed after PM resetting is executed and PM that accumulates on the element portion is removed. The detected output of the PM sensor 14 is compared with a reference output that is the basis for the determination, and if the output of the PM sensor 14 is larger than the reference output, it is determined that there is a failure in the DPF 6.

If the DPF 6 is functioning normally, a PM amount estimated to be discharged behind (downstream of) the DPF 6 in a predetermined period of time (hereinafter, also referred to as the "estimated PM discharge amount") is estimated according to a model. A reference output that is the basis for the determination is made to include an error amount and the like allowed for output according to the estimated PM discharge amount, and is set to an appropriate value. This reference output is stored in the control apparatus 16.

(4) Regeneration of the DPF 6

When the DPF 6 continues to trap PM in the exhaust gas, the amount of PM accumulated on the DPF 6 will soon reach the limit, and no more PM will be able to be trapped. In order to avoid such a state, a process for regenerating the DPF 6 by burning off the PM is performed at a stage when the PM accumulation amount of the DPF 6 has reached a certain level.

More specifically, in the regeneration process of the DPF 6, the control apparatus 16 performs control to increase the exhaust temperature according to a predetermined control program, such as control to inject fuel again after a fuel injection, and control to retard the injection timing, for example. As a result, the PM that has accumulated on the DPF 6 is burned off By executing this kind of PM burn-off for a certain period of time, a large amount of the PM that has accumulated on the DPF 6 is removed, and regeneration of the DPF to is complete.

Normally, the control apparatus 16 estimates the amount of PM that will accumulate on the DPF 6 by estimating the PM amount in the exhaust gas discharged from the internal combustion engine 2 by a model or the like. Then the regeneration process described above is performed with the timing at which the estimated amount reaches a predetermined amount as the regeneration timing of the DPF 6. Also, after the regeneration process of the DPF 6, PM resetting is executed once to remove the PM accumulated on the element portion.

Characteristic Control of the First Example Embodiment

In the first example embodiment, the SCR system 8 is arranged. With the SCR system 8, urea aqueous solution is injected from the injection valve 10 into the NOx catalyst. Ammonia ($NH_3$) is produced from the urea aqueous solution as a result of a pyrolysis reaction in Expression (1) and a hydrolysis reaction in Expression (2) below, in the PM sensor 14 and the NOx catalyst 12.

$$CO(NH_2)_2 \rightarrow NH_3 + HCNO \qquad (1)$$

$$HCNO + H_2O \rightarrow NH_3 + CO_2 \qquad (2)$$

The NOx catalyst 12 purifies the exhaust gas by reducing the NOx using the ammonia produced from the urea aqueous solution as the reducing agent, as described above.

Figure 3:
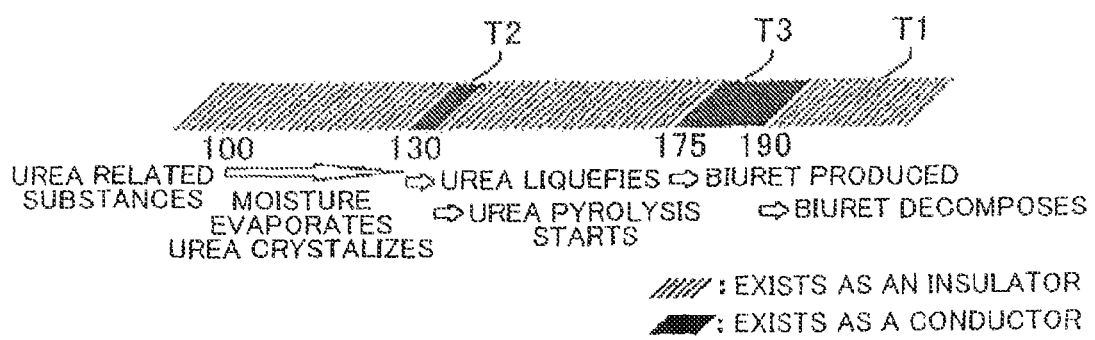
FIG. 3 is a view illustrating a change in the state of urea aqueous solution with respect temperature.

FIG. 3 is a view illustrating a change in the state of the urea aqueous solution that is a sample, with respect to temperature. As shown in FIG. 3, in a temperature range higher than 190° C., the sample sufficiently decomposes and ammonia is produced, as shown in (1), (2) above.

On the other hand, at a temperature lower than approximately 100° C., the sample exists in a liquid urea aqueous solution state, but beyond approximately 100° C., the moisture evaporates and the urea crystallizes. At this time, the sample exists as an insulator. The urea liquefies when it reaches approximately 130° C. Further, at approximately 135° C., the pyrolysis reaction (Expression (1) above) starts in the sample. In a temperature range of approximately 130 to 135° C. in FIG. 3, the urea is in a liquid state. At this time, the sample exists as a derivative. When it reaches approximately 135° C., the urea vaporizes, and the sample again becomes an insulator in a pyrolyzed state in Expression (1) above.

At approximately 160° C., a reaction takes place between the urea and isocyanic acid, and biuret ($C_2H_5N_3O_2$) starts to be produced. Moreover, the sample that includes biuret becomes a liquid in a temperature range of approximately 175 to 190° C., and the sample becomes a conductor. Then when it reaches approximately 190° C., the biuret decomposes.

In this way, when the pyrolysis reaction (1) and the hydrolysis reaction (2) of the urea aqueous solution in the NOx catalyst 12 are insufficient, substances derived from the urea aqueous solution (hereinafter, also referred to as "urea related substances"), such as urea, isocyanic acid, and biuret, are present in the NOx catalyst 12. These urea related substances may be discharged as they are downstream of the NOx catalyst 12 without being used as a reducing agent by the NOx catalyst 12. In the example embodiment below, the urea related substances derived from urea aqueous solution are not included in the PM derived from operation of the internal combustion engine 2 described above, but will be referred to separately.

When the urea related substances discharged downstream of the NOx catalyst 12 adhere to the electrodes 20, 22 of the PM sensor 14, they abruptly change the conductivity of the electrodes 20, 22 and reduce the sensitivity of the electrodes 20, 22. In this case, it is conceivable that there is no longer a correlation between the sensor output and the PM amount in the exhaust gas, that the sensor output will change abruptly regardless of a change in the PM amount, and that the sensitivity will decrease. In this kind of case, it is difficult to execute a failure determination of the DPF 6 and the like stably with high accuracy. Hence, it is desirable to remove the urea related substances adhered between the electrodes 20, 22.

Therefore, in this first example embodiment, control to increase the temperature of the element portion to a temperature at which the urea related substances can be removed is performed at a stage before execution of the failure determination control of the DPF 6. More specifically, with the control of this first example embodiment, the element portion of the PM sensor 14 is increased to a higher temperature than the decomposition temperature of biuret, such that the urea related substances decompose and are thus removed. However, it is necessary to detect the PM discharged downstream of the DPF 6 for the failure determination of the DPF 6. That is, it is necessary to leave the PM that has adhered to the element portion of the PM sensor 14. Therefore, when increasing the temperature to remove the urea related substances, the temperature is kept within a temperature that is lower than the temperature at which the PM burns.

From the above, when decomposing and removing the urea related substances, the temperature of the element portion is controlled to increase to a first temperature range T1 that is higher than the decomposition temperature of biuret and lower than the combustion temperature of PM. More preferably, the temperature of the element portion is increased such that temperature of the element portion is within a temperature range that is a temperature higher than approximately 190° C. that is the biuret decomposition temperature, and near approximately 190° C. PM burns at approximately 500° C., but if the PM adheres to the element portion is removed, an error may occur in the failure detection of the DPF 6. Also, if the element temperature becomes a high temperature, the adherability of the PM to the element portion will decrease, and the detection sensitivity of the PM sensor 14 will decrease. Therefore, in order to avoid an excessive rise in temperature, the temperature is made a temperature that is higher than the decomposition temperature (190° C.) of biuret, and a temperature that is near the decomposition temperature.

The temperature increase to the first temperature range T1 of the element portion is controlled by the energization time of the heater. That is, the energizing of the heater is controlled such that the temperature of the element portion is controlled to within the first temperature range T1 for only the period of time that it takes to burn the urea related substances. A proper energization time of the heater is obtained by testing or the like, taking the temperature change characteristics of the element portion of the PM sensor 14 into account. This value is stored in the control apparatus 16 in advance as a reference heating time.

It is known that there is a tendency for the discharge amount of the urea related substances to the downstream side of the SCR system to particularly increase in a specific operating state of the internal combustion engine 2. As a specific example, when an intake air amount G is large, for example, the flow of exhaust gas is also faster, so there is a tendency for the urea related substances to be discharged downstream of the SCR system 8. Similarly, the urea related substances tend to be discharged downstream of the SCR system 8 also when the urea equivalent ratio is high, that is, the input of urea from the injection valve 10 is large, and when the temperature of the NOx catalyst 12 is low and the like.

In this way, when the PM sensor 14 is used for equal to or longer than a certain period of time in an operating state in which the discharge amount of urea related substances tends to be large, it is predicted that the amount of urea related substances that adhere to the element portion will increase and the effect on the sensor output will be greater, in particular. Therefore, with the system of this first example embodiment, the element portion is heated to remove the urea related substances only when the cumulative time for which the PM sensor 14 has been used has reached a reference usage time (reference time) in a specific operating state in which the urea related substances tend to increase.

In this way, by executing the temperature increase control of the element portion only when adhesion of urea related substances to the element portion is predicted, the removal process of the urea related substances can be performed only when necessary, so a decrease in the sensitivity of the PM sensor 14 can be kept to a minimum, and the consumed power can be reduced.

Here, the reference usage time that will become the basis for the determination is a time close to an upper limit value of a time at which the effect on the output of the PM sensor 14 by the adhesion of the urea related substances is within an allowable range, even when the PM sensor 14 is used in an environment in which urea related substances are discharged. The specific reference usage time is obtained by testing or the like, taking into account the allowable ranges and characteristics and the like of the installed internal combustion engine 2 and SCR system, and set. This reference usage time is stored in the control apparatus 16 as a reference value for the determination.

Also, in the example embodiment, various specific operating states are conceivable, aside from when the intake air amount is large, when the urea equivalent ratio is high, and when the temperature of the NOx catalyst 12 is low, as described above. This kind of operating state is obtained by testing or the like. An operating condition to be satisfied when determining whether an operating state is a "specific operating state" based on this is set and stored in the control apparatus 16 beforehand.

Specific Control of the First Example Embodiment

Figure 4:
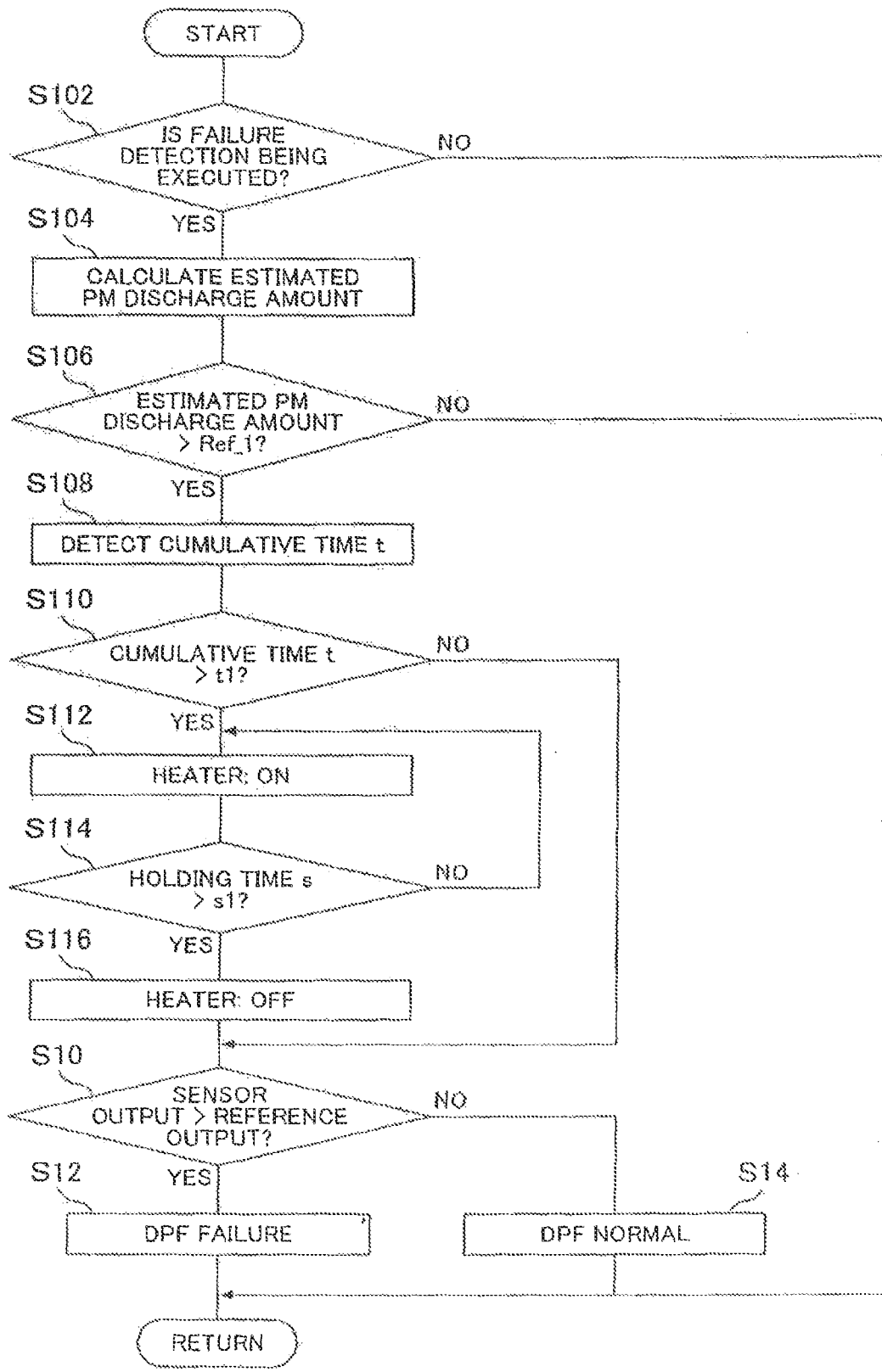
FIG. 4 is a flowchart illustrating a control routine executed by a control apparatus in a first example embodiment of the invention.

FIG. 4 is a flowchart illustrating a control routine executed by the control apparatus 16 in the first example embodiment of the invention. The routine in FIG. 4 is a routine that is repeated at regular intervals of time while the internal combustion engine 2 is operating. In the routine in FIG. 4, first, it is determined whether failure detection of the DPF 6 is currently being executed (S102). Here, a state in which failure detection of the DPF 6 is being executed is a state in which the trapping voltage is applied to the PM sensor 14 and the PM amount is being detected again after the failure determination of the DPF 6 in FIG. 4 the last time has ended, and further, after a PM reset has been executed. If the failure detection of the DPF 6 is not being executed in step S102, then this process temporarily ends.

If the failure detection of the DPF 6 is being executed in step S102, then an estimated PM discharge amount is calculated (S104). The estimated PM discharge amount is an integrated value of the PM amount estimated to have been discharged downstream of the DPF 6 from the start of the failure determination of the DPF 6 this time until the present, when the DPF 6 is functioning normally, and is estimated according to a model, with an engine speed of the internal combustion engine 2 and the like as a parameter.

Next, it is determined whether the estimated PM discharge amount has become larger than a first reference amount Ref_1 (S106). The first reference amount Ref_1 is a value that is to be the basis for determining that a PM amount of a degree that enables the output of the PM sensor 14 to be stably obtained has been discharged, according to the discharged PM amount, when PM is being discharged downstream of the DPF 6. This value is obtained by testing or the like for each PM sensor 14, and stored in the control apparatus 16. This process temporarily ends if the estimated PM discharge amount>the first reference amount Ref_1 is not satisfied in step S106.

If the estimated PM discharge amount>the first reference amount Ref_1 is satisfied in step S106, then a cumulative time t of the PM sensor 14 in the specific operating state from the start of failure detection of the DPF 6 this time until the present is read (S108). Here, the specific operating condition for determining whether the operating state is the specific operating state is set in advance, and the cumulative time t is a time counted by a time counter when this specific operating condition is satisfied. The cumulative time t starts to be cumulated when failure detection of the DPF 6 starts each time.

Next, it is determined whether the cumulative time t read in step S108 is greater than a reference usage time t1 (S110). As a result, it is able to be determined whether the PM sensor 14 has been used equal to or longer than a certain period of time in an environment in which urea related substances are discharged. The reference usage time t1 is a determination reference value that is stored in the control apparatus 16 in advance, as described above.

If the cumulative time t>reference usage time t1 is not satisfied in step S110, then it is next determined whether the sensor output is larger than a reference output (S10). The reference output is a value that is to be the basis of the determination, which is stored in the control apparatus 16 in advance as described above.

If the sensor output is larger than the reference output in step S10, it is determined that there is a failure in the DPF 6 (S12), and a predetermined control that has been set, such as illuminating a warning lamp, is executed. Then this process ends. On the other hand, if the sensor output>the reference output is not satisfied in step S16, it is determined that the DPF 6 is normal (S14). Then, this process ends. After the failure determination of the DPF, a necessary process, such as a PM reset, or a regeneration process of the DPF 6 or the like, is executed at a predetermined timing before the next failure determination of the DPF 6.

On the other hand, if the cumulative time t>reference usage time t1 is satisfied in step S110, then the heater is turned ON (S112). That is, here, a predetermined power is supplied to the heater in response to a control signal from the control apparatus 16 to energize the heater. As a result, the element portion starts to be heated.

Next, it is determined whether a holding time a after the heater has been turned ON in step S112 is longer than a reference heating time s1 (S114). The reference heating time s1 is a determination reference value that is stored in the control apparatus 16 in advance as a period of time necessary for the temperature of the element portion to rise to the first temperature range T1. Therefore, if the holding time s>the reference heating time s1 is not satisfied in step S114, the process returns to S112 again and the heater ON state is maintained, and it is determined whether the holding time s>the reference heating time s1 is satisfied in step S114.

If it the holding time s>the reference heating time s1 is satisfied in step S114, it is thought that the temperature of the element portion has risen to the first temperature range T1, so the heater is turned OFF (S116). In this state, it is thought that the urea related substances adhered to the element portion of the PM sensor 14 have been removed by the heating of the element portion. Therefore, the process then proceeds to S10, and a determination as to whether there is a failure in the DPF 6 is made according to the processes in S10 to S14. After the failure determination of the DPF 6, a necessary process, such as a PM reset or regeneration process of the DPF 6 or the like, is executed at a predetermined timing before the next failure determination of the DPF 6.

As described above, according to this first example embodiment, when the PM sensor 14 is exposed for a certain period of time to an environment in which urea related substances are discharged, a determination as to whether there is a failure in the DPF 6 is made after a process to remove the urea related substances is performed. Therefore, the output of the PM sensor is able to be obtained in a state in which the urea related substances that affect the sensor output have been removed, so the accuracy of the failure detection of the DPF 6 can be further improved.

Figure 5:
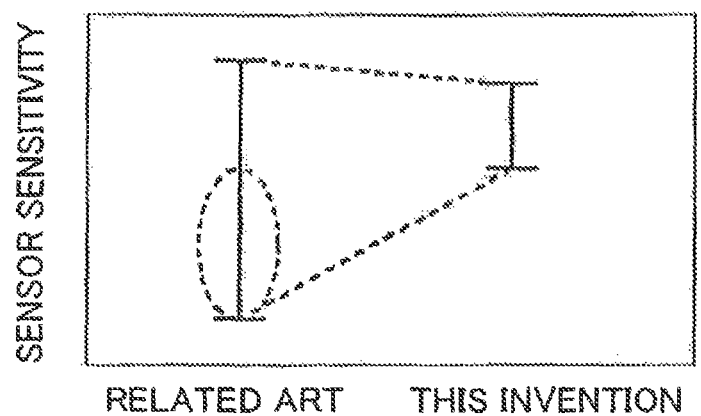
FIG. 5 is a view illustrating output variation of the PM sensor of the first example embodiment of the invention, compared to that of a related PM sensor.

FIG. 5 is a view comparing variation in the sensitivity of the PM sensor 14 when the control of the first example embodiment is performed, to variation in the sensitivity of a PM Sensor when the control of the first example embodiment is not performed, when gas with the same PM amount is detected. From FIG. 5 as well, it is evident that the variation in the sensitivity of the sensor is suppressed, so high sensitivity is able to be maintained, according to the control of this first example embodiment.

In this first example embodiment, a case will be described in which only when the estimated PM discharge amount>the first reference amount Ref_1 is satisfied in step S106, are the processes thereafter performed. However, in this invention, the order of the processes is not limited to this. For example, the determination as to the cumulative time t>reference usage time t1 may be made first, then a determination as to whether the estimated PM discharge amount is greater than the predetermined reference value may be made in both cases in which this determination is satisfied and not satisfied, and according to each of these, the process may proceed on to the temperature increasing process (S112, S114) or the determination as to whether there is a failure (S10 to S14). This is also the same in second and third example embodiments.

Also, in the first example embodiment, a case was described in which only when the estimated PM discharge amount>the first reference amount Ref_1 is satisfied, are the processes thereafter performed. However, this invention is not limited to this. For example, when an elapsed time after failure detection starts reaches a predetermined period of time, the processes thereafter may be proceeded with. Here, the predetermined period of time is set to a sufficient period of time until the PM sensor 14 generates a stable output with respect to the PM amount discharged to the downstream side, when there is a failure in the DPF 6. This is also the same in the second and third example embodiments.

Also, a case was described in which the heater is kept ON for a certain period of time, as a process for removing the urea related substances. However, the control for removing the urea related substances is not limited to this. For example, after turning the heater ON, the temperature of the element portion may also be monitored. In this case, it would be determined whether the temperature of the element portion has reached the first temperature range T1, and if the temperature of the element portion has reached the first temperature range T1, the next process would be proceeded with. A temperature sensor may also be provided and the temperature of the element portion may be detected directly, or the heating temperature may be controlled by detecting the resistance or impedance of the heater or the like. This is also the same in the second and third example embodiments.

Also, in this first example embodiment, a case was described in which during the control of the failure determination of the DPF 6, a determination, is made as to whether the cumulative time t>the reference usage time t1 is satisfied in step S110, and if it is satisfied, temperature increase control of the element portion is performed, and then continuing on, a determination as to whether there is a failure in the DPF 6 (S10 to S14) is made. However, the invention is not limited to this. For example, the determination of whether the cumulative time t>the reference usage time t1 is satisfied (S108, S110) and the temperature increase control (S112 to 116) may also be executed as a separate routine from the failure determination control.

More specifically, a failure determination control routine including steps S102, S104, S106, and S10 to S14, for example, is prepared, and repeatedly executed at regular intervals of time. On the other hand, a routine that includes determining the cumulative time and performing a temperature increasing process for removing urea related substances, which includes steps S108, S110, and S112 to S116, is prepared, and repeatedly executed separately at regular intervals of time. Also, if the cumulative time t>the reference usage time t1 is satisfied in S110, a process to prohibit the failure determination of the DPF 6 according to steps S10 to S14 of the failure determination control is performed until the temperature increasing process of steps S112 to S116 is complete. In this way as well, when it is predicted that urea related substances are adhered, the urea related substances are able to be removed, so an erroneous determination in the failure determination of the DPF 6 is able to be inhibited. This is also the same in the second and third example embodiments.

Also, in the first example embodiment, control of the failure determination of the DPF 6 was given as control that is started after the temperature increasing process of the PM sensor 14, or control that is prohibited until the temperature increase is complete. However, in this invention, the control that is started after the temperature increasing process, or control that is prohibited until the temperature increase is complete, is not limited to this, but may be other control related to the DPF 6. This is also the same in the second and third example embodiments.

Second Example Embodiment

A system of a second example embodiment has the same structure as the system in FIG. 1, except for that it is provided with an EGR system, and a function of being able to electronically control an accelerator opening amount. In the system of the second example embodiment as well, when the cumulative time t in the specific operating state of the internal combustion engine 2 is longer than the reference usage time t1, control to increase the temperature of the element portion to the first temperature range T1 is executed to remove urea related substances, similar to the first example embodiment. However, in this second example embodiment, the environment and the like in which the process to increase the temperature of the element portion is executed is limited in the manner described below.

When the temperature of the element portion increases due to the temperature increasing process for removing urea related substances, the amount of PM adhered to the element portion of the PM sensor 14 decreases. Therefore, when the temperature increasing process is executed in an environment in which the PM discharge amount is large, there may be a large difference between the actual output of the PM sensor 14 and the actual PM discharge amount, at the time of the failure determination, due to a decrease in sensitivity of the PM sensor 14 resulting from the temperature increasing process.

Therefore, with the system of the second example embodiment, the temperature increasing process for removing urea related substances is executed in an environment in which the PM amount that is able to be discharged from the internal combustion engine 2 is small. More specifically, the temperature increasing process is executed when an estimated value of the PM discharge amount per instantaneous short period of time (hereinafter, also referred to as "estimated instantaneous PM amount") is smaller than a second reference amount Ref_2. This second reference amount Ref_2 is a value that is to be the basis for determining whether the operating state is one in which the amount of PM able to be discharged is small. Here, the second reference amount Ref_2 is an upper limit value of an amount such that output variation of the PM sensor due to a decrease in output sensitivity will be within an allowable range, even if the temperature of the PM sensor 14 has increased in a state in which PM of that amount has been discharged downstream of the DPF 6, and is obtained by testing or the like in advance, and set.

Moreover, when the temperature increase control is executed in this kind of environment, recirculation of exhaust gas by an EGR system is stopped when there is a load change. Also, simultaneously, an accelerator opening amount change amount is controlled to change in a range less than a certain value. As a result, even if the load becomes large, a decrease in torque is able to be inhibited and an emission increase is able to be suppressed, and urea related substances are able to be removed.

Figure 6:
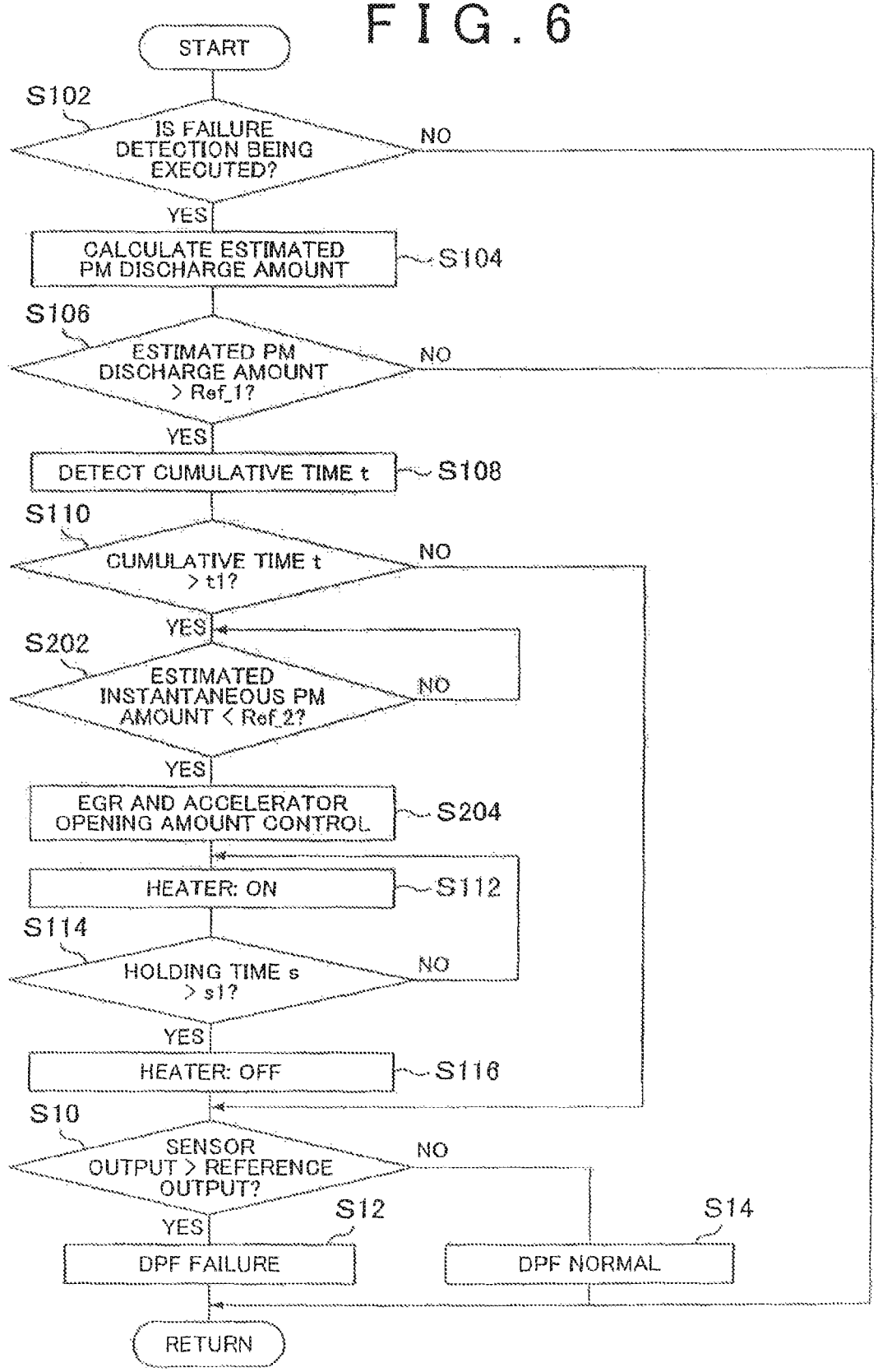
FIG. 6 is a flowchart illustrating a control routine executed by a control apparatus in a second example embodiment of the invention.

FIG. 6 is a flowchart illustrating a control routine executed by the control apparatus 16 in the second example embodiment of this invention. The routine in FIG. 6 differs from the routine in FIG. 4 only in that the processes of S202 to S204 are provided between the process of S110 and the process of S112 in the routine in FIG. 4.

More specifically, in this routine, if the cumulative time t of the PM sensor 14 in a specific operating state is larger than the reference usage time t1 (S110), then it is determined whether the estimated instantaneous PM amount is smaller than the second reference amount Ref_2 (S202). Here, the estimated instantaneous PM amount is a value that is calculated from the current operating state. The second reference amount Ref_2 is stored in the control apparatus 16 in advance, and is a value that is the basis for determining whether the operating state is one in which the PM amount that is able to be discharged is large.

If the estimated instantaneous PM amount<the second reference amount Ref_2 is not satisfied in step S202, then the process of step S202 is repeated until the estimated instantaneous PM amount<the second reference amount Ref_2 is satisfied in step S202.

On the other hand, if the estimated instantaneous PM amount<the second reference amount Ref_2 is satisfied in step S202, then next in step S204, a process for turning the EGR OFF and limiting the accelerator opening amount change amount to a range less than a certain value is executed. The ON and OFF of the EGR, and the accelerator opening amount are controlled by a separately set control program.

Here, when necessary, in that control program, the EGR is turned OFF and the amount of change in the accelerator opening amount is limited.

Then, a temperature increasing process of the element portion in steps S112 to S116, and a process for determining whether there is a failure in the DPF 6 in S10 to S16 are executed similar to the routine in FIG. 4.

As described above, in the processes of this second example embodiment, the urea related substances removal process by heating the element portion is executed only in an environment in which the estimated instantaneous PM amount is less than the second reference amount Ref_2. As a result, the effect of decreasing the output sensitivity of the PM sensor 14 due to the increase in temperature of the element portion is reduced, so more accurate output of the PM sensor 14 can be obtained.

Also, when there is a load change when heating the element portion, the EGR is turned OFF and the amount of change in the accelerator opening amount is controlled to be less than a certain value. As a result, the element portion temperature increasing process can be performed in an environment in which the PM discharge amount is low, so more accurate output of the PM sensor can be obtained, while inhibiting a decrease in torque and an increase in emissions and the like.

Third Example Embodiment

A system and PM sensor of a third example embodiment have similar structures as the PM sensor in FIG. 1 and FIG. 2. In the system of the third example embodiment, a process to maintain a state in which substances exist particularly as liquid, of the urea related substances, is executed in addition to the element portion temperature increasing process, which is performed at a timing before the DPF 6 failure detection, of the first or second example embodiment.

More specifically, as described above, when a specific operating state in which the discharge amount of urea related substances is large is anticipated, with the system of the third example embodiment, a process for inhibiting urea related substances that are liquid from adhering to the element portion beforehand is executed. More specifically, in a specific operating state in which an increase in the discharge amount of urea related substances is anticipated, the temperature of the element portion is controlled so as not to be in a second temperature range T2 of 130 to 150° C. that is a liquid phase temperature of urea, or a third temperature range T3 of 175 to 190° C. that is a temperature range before the decomposition of biuret. As a result, the adhesion of conductive urea related substances that are liquid that particularly affects the sensor output is prevented in advance, so variation in sensor output can be suppressed.

Figure 7:
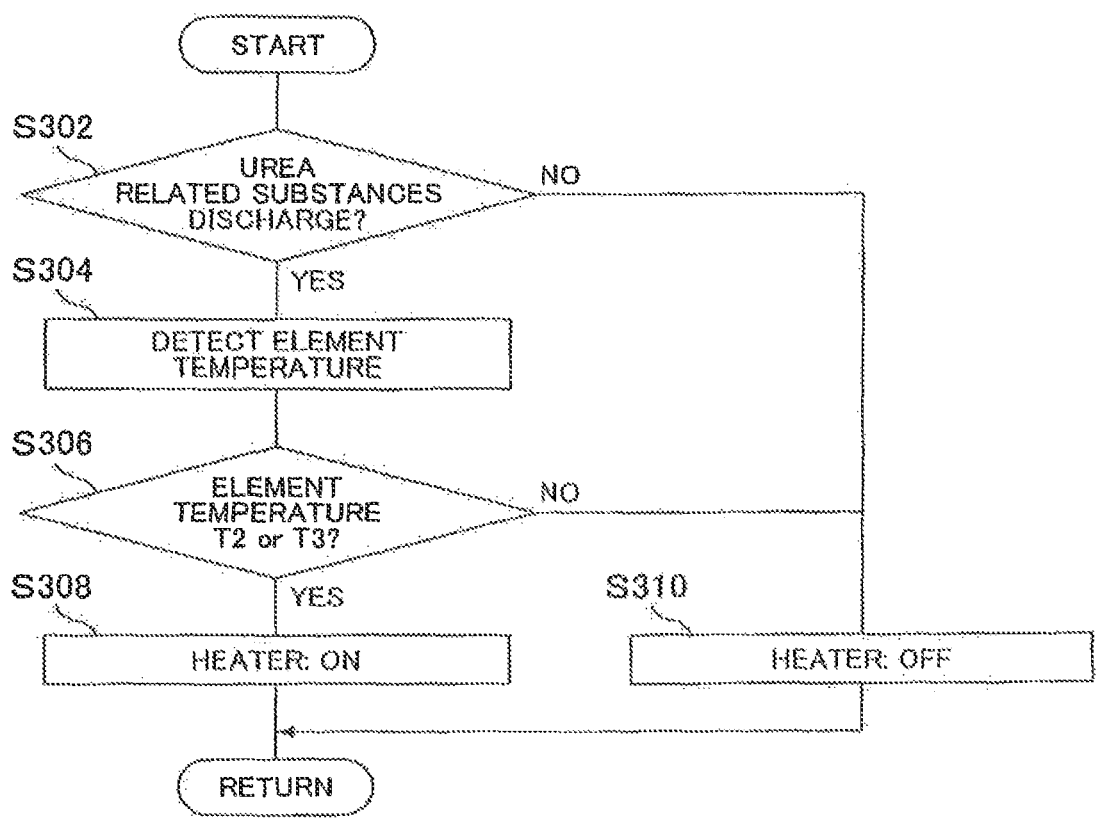
FIG. 7 is a flowchart illustrating a control routine executed by a control apparatus in a third example embodiment of the invention.

FIG. 7 is a flowchart illustrating a control routine executed by a control apparatus in the third example embodiment of this invention. The routine in FIG. 7 is able to be executed before the failure determination of the DPF 6 is executed, when the cumulative time t>reference usage time t1 is not satisfied in step S106 in the routines in FIG. 4 and FIG. 6.

More specifically, in the routine in FIG. 7, first, it is determined whether the operating state is currently a specific operating state in which discharge of urea related substances is anticipated (S302). A condition for the specific operating state in which the discharge of urea related substances is anticipated is stored in the control apparatus 16 in advance. Therefore, here, it is determined whether the operating state is one in which the condition stored in the control apparatus 16 is satisfied.

If in step S302 discharge of urea related substances is not anticipated, this process ends. On the other hand, if the environment is one in which urea related substances is discharged in step S302, then the current temperature of the element portion is detected (S304). Here, the temperature of the element portion is obtained by detecting the resistance in the heater.

Next, it is determined whether the temperature of the element portion is a temperature that is within the second temperature range T2 or the third temperature range T3 (S306). The second temperature range T2 is a liquid phase temperature range of urea, and the third temperature range T3 is a temperature range before the decomposition of biuret. If the temperature is not within the second temperature range T2 or within the third temperature range T3 in step S306, the heater is turned OFF (S308). Then this process ends.

On the other hand, if the element temperature is within the second temperature range T2 or within the third temperature range T3 in step S306, then the heater is energized for a certain period of time, and the temperature of the element portion is increased (S310). As a result, if the temperature is in the second temperature range, for example, the temperature of the element portion is controlled to within a range higher than the second temperature range T2 and lower than the third temperature range T3, or to a first temperature range T1 that is a higher temperature than the third temperature range t3. Also, if the temperature of the element portion is within the third temperature range T3, the temperature of the element portion is controlled to the first temperature range T1. Here, the temperature is controlled by the energization time of the heater. The energization time of the heater is set to an appropriate time in advance, such that the element portion becomes the appropriate temperature. As a result, urea related substances in a conductor state that greatly affects the output are able to be removed from the element portion. Then this process ends.

Also, the routine of this third example embodiment may also be executed before starting the routines in FIGS. 4 and 6, for example. As a result, even if the environment is one in which urea related substances tend to be discharged, control is performed in advance so that the urea related substances will not easily adhere to the element portion. Therefore, for example, the reference usage time t1 in step S110 may also be set long, so the number of times that the temperature of the element portion is increased to the high first temperature range in order to remove the urea related substances is able to be kept down.

Also, this routine may also be executed independently as appropriate, in an environment in which the adhesion of urea related substances is undesirable, irrespective of the routines in FIG. 4 and FIG. 6. As a result, it is possible to effectively inhibit urea related substances present in a conductor state from adhering to the element portion of the PM sensor 14 as necessary.

Also, when numbers such as ranges, amounts, quantities, and number of various elements are cited in the example embodiments described above, the invention is not limited to those cited numbers, except when specifically specified and when clearly identified as that number in principle. Also, the structure and structural process and the like described in this example embodiment are not absolutely essential to this invention, except when particularly specified and when identified as such in principle.

DESCRIPTION OF THE REFERENCE NUMERALS

2 INTERNAL COMBUSTION ENGINE
4 EXHAUST PATH
8 SCR SYSTEM
10 INJECTION VALVE
12 NOx CATALYST
14 PM SENSOR
16 CONTROL APPARATUS
18 INSULATING SUBSTRATE
20, 22 ELECTRODES
t1 REFERENCE USAGE TIME (REFERENCE TIME)
Ref1 FIRST REFERENCE AMOUNT
Ref2 SECOND REFERENCE AMOUNT
T1 FIRST TEMPERATURE RANGE
T2 SECOND TEMPERATURE RANGE
T3 THIRD TEMPERATURE RANGE

The invention claimed is:

1. A control apparatus of an internal combustion engine comprising:
a controller that detects an amount of particulates derived from operation of the internal combustion engine, inside of an exhaust path of the internal combustion engine, based on an output of a particulate sensor arranged downstream of a SCR system arranged in the exhaust path, and that controls a temperature of an element portion of the particulate sensor, wherein
when a cumulative value of a time for which the particulate sensor is used in a specific operating state in which urea related substances are discharged to a downstream side of the SCR system reaches a reference time after detection of the particulate amount by the particulate sensor has started this time, the controller performs control to increase the temperature of the element portion of the particulate sensor to a first temperature range that is a temperature that is higher than a temperature at which the urea related substances decompose, and lower than a temperature at which the particulates are burned off.

2. The control apparatus of the internal combustion engine according to claim 1, wherein:
a particulate filter for trapping the particulates is arranged upstream of the particulate sensor in the exhaust path; and
the controller prohibits a predetermined control related to the particulate filter, until the temperature of the element portion reaches the first temperature range.

3. The control apparatus of the internal combustion engine according to claim 1, wherein:
a particulate filter for trapping particulates in exhaust gas is arranged upstream of the particulate sensor in the exhaust path; and
the controller starts a predetermined control related to the particulate filter, after the temperature of the element portion has reached the first temperature range.

4. The control apparatus of the internal combustion engine according to claim 2, wherein the predetermined control is failure determining control that determines whether there is a failure in the particulate filter, based on the output of the particulate sensor.

5. The control apparatus of the internal combustion engine according to claim 1, wherein the controller performs a control to increase the temperature of the element portion, when the internal combustion engine is in an operating state in which the amount of the particulates discharged is less than a reference amount.

6. The control apparatus of the internal combustion engine according to claim 5, wherein:
the internal combustion engine includes an EGR system; and the controller stops recirculation of exhaust gas by the EGR system when a change in a load during operation of the internal combustion engine is larger than a predetermined change.

7. The control apparatus of the internal combustion engine according to claim 5, wherein the controller limits an accelerator opening amount change amount to within a predetermined range that is smaller than a normal change amount of an accelerator opening amount, when a change in a load during operation of the internal combustion engine is larger than a predetermined change.

\* \* \* \* \*